United States Patent [19]

Molina

[11] 4,035,641

[45] July 12, 1977

[54] LIQUID OXYGEN COMPATIBLE BIODEGRADABLE DYE PENETRANT COMPOSITIONS AND METHOD OF DYE

[75] Inventor: Orlando G. Molina, Westminster, Calif.

[73] Assignee: Rockwell International Corporation, El Segundo, Calif.

[21] Appl. No.: 707,160

[22] Filed: July 21, 1976

[51] Int. Cl.$^2$ .................................... G01N 21/16
[52] U.S. Cl. .............................. 250/302; 73/104; 252/301.19
[58] Field of Search .................... 250/302, 301.19; 73/104

[56] References Cited

U.S. PATENT DOCUMENTS

| | | | |
|---|---|---|---|
| 3,716,492 | 2/1973 | Graham et al. | 250/302 X |
| 3,981,185 | 9/1976 | Molina | 250/302 X |
| 3,989,949 | 11/1976 | Molina | 250/302 |
| 3,995,157 | 11/1976 | Holub et al. | 250/302 |

*Primary Examiner*—Archie R. Borchelt
*Attorney, Agent, or Firm*—C. T. Silberberg; L. Lee Humphries

[57] ABSTRACT

Liquid oxygen-compatible water washable substantially biodegradable dye penetrant composition having excellent sensitivity and high stability, for use in non-destructive dye penetrant inspection particularly of parts or mechanical components which are later placed in contact with liquid oxygen, and which are compatible with a wide variety of metals including steel alloys, such composition consisting essentially of an organic dye, preferably a fluorescent dye, a carrier or solvent for said dye, in the form of certain oxyalkylated alcohols, preferably ethoxylated linear alcohols, particularly the biodegradable nonionic surfactants comprised of ethoxylates of a mixture of secondary alcohols having linear alkyl chains of from 11 to 15 carbon atoms, and an average of from 3 to 12 moles of ethylene oxide, and a nonhalogenated solvent which is volatile at room temperature, e.g. a ketone such as methyl ethyl ketone or acetone, or a suitable alcohol such as ethyl alcohol. In the method of application of the dye penetrant composition, such composition is applied to the surface of an object containing cracks and flaws, and following rapid evaporation of the solvent, water is applied to the surface of the object to remove excess liquid dye penetrant composition from the surface without removing such penetrant from the cracks and defects, and with or without a developer, the surface of the object is viewed under suitable lighting conditions, e.g. ultraviolet or black light when the dye in the penetrant is a fluorescent dye, to locate any cracks or defects in the surface of the body as indicated by colored traces from the dye penetrant remaining in the cracks and flaws. Upon evaporation of the solvent, residual dye penetrant remaining on the object surface is rendered nonsensitive or nonreactive with liquid oxygen.

48 Claims, No Drawings

LIQUID OXYGEN COMPATIBLE BIODEGRADABLE DYE PENETRANT COMPOSITIONS AND METHOD OF DYE

BACKGROUND OF THE INVENTION

This invention relates to an improved liquid oxygen (LOX) compatible biodegradable dye penetrant composition and method for non-destructively testing material specimens to locate and identify surface voids, cracks or defects, prior to contacting such parts with liquid oxygen. The invention is especially concerned with a novel generally easily water washable, stable and sensitive dye penetrant composition of the above type having the characteristics of being able to disclose a wide range of defective conditions in parts, employing as solvent or vehicle essentially a biodegradable nonionic surfactant in the form of certain oxyalkylated alcohols, preferably ethoxylated alcohols, and mixtures thereof, and incorporating an additive to render the composition compatible with liquid oxygen (LOX); and to a method utilizing such dye penetrant composition for nondestructive testing of parts subsequently contacted with liquid oxygen.

Dye penetrants are highly useful materials for nondestructive testing of metal work piece surfaces. In many important and expensive mechanical devices, it is necessary to inspect every metal component of the system for structural defects, prior to final fabrication. Dye penetrants are particularly useful in decreasing inspection processing time and can be highly sensitive in detecting microdefects in metal components of aluminum, steel, nickel, titanium and the like.

In known penetrant inspection methods for rapid location and evaluation of surface flaws or cracks in test bodies or parts, a dye penetrant composition, preferably containing a fluorescent dye, and which will penetrate the openings of the surface cracks or flaws in the part, is applied to the surface of the test body, and the excess penetrant composition is removed from the surface of the body. A developer composition may then be applied to the part surface, which acts as a wick and causes the liquid penetrant containing the fluorescent dye, which was retained in the cracks or surface flaws, to be drawn up out of the surface defects by capillary action. The part is then exposed to appropriate lighting conditions, such as invisible fluorescigenous light, and the location of the surface flaws is revealed by the emission of visible fluorescent light by the penetrant dye which was retained in the cracks or flaws after the penetrant composition was removed from the surface of the part.

For best efficiency, particularly for the detection and location of minute surface cracks and flaws, as well as intermediate size and gross cracks, it is necessary that the dye penetrant have high sensitivity.

In addition, stability of the penetrant solution is essential without the necessity for carefully balancing the various liquid components of a dye penetrant solution in order to obtain efficient penetration of the solution into the cracks and flaws of a part, dye solubility, wetting action and washability control.

An additional criterion has recently developed also with respect to dye penetrant solutions and compositions. Generally, dye penetrant solutions presently being used and containing solvents and wetting agents present a disposal problem in that they are substantially non-biodegradable, that is, they are very difficult to decompose by bacteria in sewage disposal plants. Hence the necessity for the development of dye penetrant solutions and compositions which are biodegradable, that is which employ dye solvents and carriers which are biodegradable, and are readily available despite the petrochemical shortage, has attained considerable importance.

In my U.S. Pat. Nos. 3,915,885 and 3,915,886, there are disclosed novel dye penetrants which have improved washability and sensitivity characteristics, and which are biodegradable, containing as the vehicle for the dye, certain biodegradable nonionic oxyalkylated alcohols.

Further, where the parts to be inspected are to be later subjected to contact with LOX or a like strong oxidizer, it is particularly desirable that the inspection system, and the dye penetrants used in inspection do not increase the danger or sensitivity of the mechanical components to reaction with such strong oxidizers including LOX. For example, a large rocket propellant motor may use LOX, or a like strong oxidizer, in the rocket propellant. It is quite important under these circumstances that the LOX not be reactive with any traces or residues of the inspection dye penetrant which may remain in the cracks or defects of the inspected propellant tanks or other components, fabricated from inspected metal stock after cleaning.

In my U.S. Pat. No. 3,753,647 there is disclosed a liquid dye penetrant which is compatible with liquid oxygen and which comprises N-methyl-2-pyrrolidone, a mixture of a ketone and wetting agents, a fluorescent dye and a halocarbon. Although such dye penetrant composition has been found effective, it has the disadvantages of requiring a multiplicity of dye carriers or solvents, with proper balance thereof necessary to provide a desired sensitivity, and the composition is not biodegradable.

In my copending application Ser. No. 577,958, filed May 15, 1975, now U.S. Pat. No. 3,989,949, there is disclosed an improved liquid oxygen compatible dye penetrant which is biodegradable, employing as solvent or carrier for the dye certain biodegradable nonionic surfactants comprised of ethoxylated liner alcohols as described in my U.S. Pat. No. 3,915,886, and a halocarbon.

However, both of the above described dye penetrants containing a halocarbon, particularly a chlorinated hydrocarbon, and which are nonflammable type solvents, are incompatible for use with certain metals, particularly with steel surfaces, which are sensitive to attack by chlorinated hydrocarbons.

Accordingly, an object of the present invention is the provision of a readily water washable biodegradable liquid oxygen compatible dye penetrant solution or composition which is of simple formulation and which does not require the use of mixtures of conventional solvents and wetting agents, and which is formed of an essentially single or sole nonionic surfactant, and which is highly stable, has excellent sensitivity and is essentially non-toxic. A particular object of the invention is to provide a dye penetrant solution of the above noted type, and which incorporates a nonhalogenated additive which eliminates the hazard of traces of dye penetrant reacting explosively with liquid oxygen or other strong oxidizers, substantially, without affecting the biodegradability or sensitivity of the dye penetrant, such additive being of a type rendering such dye penetrant compatible with a wide range of metal surfaces including steel alloys. A still further object is the provision of procedure employing such novel biodegradable and LOX safe dye penetrant composition for inspection of cracks, flaws and metallurgical conditions in metal structural components which are later to be placed in contact with liquid oxygen.

DESCRIPTION OF THE INVENTION

It has now been found that the above objects and advantages can be accomplished according to the invention, and an improved LOX and gaseous oxygen compatible liquid dye penetrant, having good sensitivity for detection of cracks and defects in metal surfaces, and which is biodegradable, is provided by employing as a solvent or carrier for the dye, e.g. fluorescent dye, certain biodegradable nonionic surfactants comprised of certain oxyalkylated alcohols, of the type disclosed in my U.S. Pat. Nos. 3,915,885 and 3,915,886, separately or in admixture, and a non-halogenated organic solvent which is volatile at room temperature, particularly a ketone or an alcohol. Such dye penetrants are compatible with metals, particularly those employed in the aircraft industry, including steel alloys. It was particularly unexpected to find that although such halogen-free volatile solvents are generally flammable, and reactive to liquid oxygen, when employed in substantial proportions in conjunction with the basic dye penetrant containing the above biodegradable surfactant as vehicle, and a dye, the residue of the resulting dye penetrant composition is compatible with liquid oxygen (LOX). The biodegradable nonionic surfactant employed essentially as the sole solvent or carrier for the dye preferably comprises ethoxylates of a mixture of linear secondary aliphatic alcohols having linear alkyl chains of from 11 to 15 carbon atoms, and an average of from 3 to 12 moles of ethylene oxide, as described in my Pat. No. 3,915,886.

The dye penetrant composition of the invention contains a large or major proportion of the nonhalogenated volatile solvent, e.g. ketone, and upon application of the composition to a part surface, for example, the metal components of a rocket motor system which employs LOX as an oxidizer in rocket liquid propellants, it has been found that such solvent rapidly volatilizes at room temperature and the organic residue in the cracks and flaws of the part or component following inspection thereof, does not react chemically or explosively, with the liquid or gaseous oxygen in contact with the metal surfaces of the rocket motor system. On the other hand, in the absence of such solvent in the dye penetrant composition, such residue can react violently with liquid oxygen, as noted below.

In addition, due to the rapid and substantially complete volatility of the nonhalogenated volatile solvent following application of the penetrant to a part surface, the biodegradability of the remaining dye penetrant, in the absence of solvent, is not altered or affected, and moreover, the initial presence of the solvent in the dye penetrant does not affect the sensitivity of the dye penetrant following removal of such solvent.

The nonionic biodegradable solvent or carrier employed essentially as the sole vehicle for the dye of the dye penetrant composition according to the invention can be alkylene oxide condensation products prepared by the reaction of an organic compound having a reactive hydrogen atom, such as an aliphatic alcohol, with ethylene oxide, propylene oxide, or mixtures thereof.

Thus, the biodegradable nonionic surfactant consists essentially of an oxyalkylated aliphatic alcohol or mixtures thereof, formed of an aliphatic primary or secondary alcohol carrying ethoxy or propoxy groups, including polyoxyethylene or polyoxypropylene groups, or mixtures thereof.

More particularly, one class of such nonionic solvents or carriers can be defined as straight chain, primary, aliphatic oxyalkylated alcohols, generally in the form of mixtures thereof, wherein the primary aliphatic alcohols can have from 8 to 20 carbon atoms, preferably 10 to 18 carbon atoms, and the oxyalkyl groups are ethylene oxide and propylene oxide, preferably in the form of a mixture thereof.

One class of nonionic carriers within the class of materials defined immediately above is a cogeneric mixture of compounds represented by the formula:

wherein:

R is an essentially linear alkyl group having from 10 to 18 carbon atoms, with the proviso that at least 70 weight percent of said compounds in said mixture have an R of from 12 to 16 carbon atoms, and A is a mixture of oxypropylene and oxyethylene groups, said oxypropylene and oxyethylene groups being from 55 to 80% of the total weight of the compounds, the oxypropylene to oxyethylene ratio of said total weight being from 0.85:1 to 2.75:1, preferably 1.25:1 to 2.25:1.

Another preferred class of condensation products or oxyalkylated alcohols within the above definition are those wherein the aliphatic alcohols of the oxyalkylated alcohols, or R in the above formula, ranges from 12 to 18 carbon atoms, and the total number of ethylene oxide and propylene oxide groups in the mixture thereof, or designated A in the above formula, ranges from about 4 to about 14.

The term "cogeneric mixture" as employed herein, designates a series of closely related homologues obtained by condensing a plurality of oxide units, with an alcohol or a mixture thereof. As is known, when a mixture of this type is generated, various oxyalkylene chain lengths are obtained.

Alcohols which may be employed in the preparation of the products noted above are those essentially linear, primary, aliphatic alcohols having from 8 to 20 carbon atoms, preferably 10 to 18 carbon atoms. Mixtures of alcohols are usually preferred since their use provides for a good balance of properties in the resulting products. Examples of alcohols which are operable include decyl alcohol, undecyl alcohol, lauryl alcohol, tridecyl alcohol, tetradecyl alcohol, pentadecyl alcohol, cetyl alcohol, heptadecyl alcohol, stearyl alcohol, hydrogenated tallow alcohol, and mixtures thereof. They may be naturally-derived such as from coconut oil or synthetically-derived such as from linear alkanes or linear olefins.

The nonionic biodegradable surfactants employed as carrier or vehicle for the dye of the penetrant solution according to the invention, are prepared by condensing an alcohol or mixture of alcohols, as described above, with a mixture of ethylene oxide and propylene oxide, in the presence of an alkyline catalyst, such as potassium hydroxide. The oxide mixture may be added to the alcohol in one continuous step or it may be added in several steps. The products thus provided possess random distribution of oxyethylene and oxypropylene groups.

The nonionic surface active agents described above and their method of preparation are disclosed in U.S. Pat. No. 3,504,041, and such disclosure is incorporated herein by reference. These surface active agents are believed to include, for example, that class of surfactants which are marketed as the "Plurafac" surfactants "RA-40" grades.

Another class of biodegradable liquid, water miscible oxyalkylated alcohol condensation products within the above definition are those wherein the aliphatic alcohol, or R, is a straight chain alkyl group having from 8 to 20 carbon atoms, the number of ethylene oxide groups in the mixture thereof with propylene oxide, or A, ranges from 3.75 to 12.75, and the number of propylene oxide groups in such mixture ranges from 1.7 to 7.0, the oxyethylene to oxypropylene ratio in such mixtures being from 1.8:1 to 2.2:1. Such cogeneric mixtures can be prepared in two steps, the first step being condensation of an alcohol mixture and ethylene oxide in the presence of an alkaline condensing agent or catalyst, to form an ethoxylated product, followed by condensing the resulting ethoxylated product with propylene oxide. There can be employed in such reaction a mixture of straight chain aliphatic alcohols having from 8 to 20 carbon atoms in the aliphatic chain. This cogeneric mixture of condensation products and the method of their preparation are disclosed in U.S. Pat. No. 3,340,309, and such disclosure is also incorporated herein by reference. The nonionic oxyalkylated alcohols marketed as the "RA-20" grades of "Plurafac", are believed representative of the class of surface active agents disclosed in the latter patent.

Various other Plurafac grades which are marketed and are believed to be generally within the above-described classes of oxyalkylated alcohol surfactants are those designated RA-43, A-24, A-25, B-25-5, B-26 and D-25.

Dye penetrant compositions containing the above described primary aliphatic oxyalkylated alcohols as vehicle, and a dye are described in my above U.S. Pat. No. 3,915,885.

A class of particularly preferred nonionic biodegradable solvents or carriers which can be employed as substantially the sole vehicle for the dye of the dye penetrant compositions according to the present invention are ethoxylates of a mixture of linear secondary aliphatic alcohols, with the hydroxyl groups randomly distributed, the linear aliphatic hydrophobic portion of such alcohols being a mixture of alkyl chains containing in the range from 10 to 17 carbon atoms, preferably from 11 to 15 carbon atoms, and containing an average of from 3 to 12 moles of ethylene oxide.

The above particularly preferred class of nonionic biodegradable surfactant employed as carrier for the dye penetrant of the invention is a mixture of compounds which can be represented by the formula:

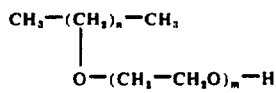

where n is in the range from 9 to 13, and m is 3 to 12.

Although preferably each of the above-defined surfactants is formed of a mixture of two or more linear alkyl hydrophobic chains ranging from $C_{11}$ to $C_{15}$, as noted below, the surfactant can contain a single such chain formed from a single secondary aliphatic alcohol of the types described below.

The linear alkyl hydrophobic portion of the above defined surfactant is a mixture of $C_{11}$ to $C_{15}$ linear alkyl chains, and can be derived from a mixture of $C_{11}$ to $C_{15}$ aliphatic secondary alcohols, for example the secondary undecyl, dodecyl, tridecyl, tetradecyl and pentadecyl alcohols. The hydrophilic portion of the surfactant is a polyoxyethylene chain randomly attached to any carbon atom of the linear alkyl hydrophobic chains, other than to the terminal carbon atoms thereof, through an ether linkage. It will accordingly be understood that the specific carbon atom in the alkyl hydrophobic chains to which the hydrophilic polyoxyethylene chain is attached will become a

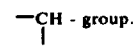

Such hydrophilic polyoxyethylene chain is generally expressed in terms of an average number of moles of ethylene oxide.

Illustrative examples of biodegradable nonionic surfactants of the types defined in the above formula are those consisting of a mixture of ethoxylates of from 11 to 15 carbon atoms in the aliphatic hydrophobic chain, and which have an average of 3, 5, 7, 9 and 12 moles of ethylene oxide, respectively, as the hydrophil.

Materials corresponding to these five examples of biodegradable nonionic surfactants are marketed, respectively, as:
Tergitol 15-S-3
Tergitol 15-S-5
Tergitol 15-S-7
Tergitol 15-S-9
Tergitol 15-S-12

In each case of the Tergitol S series of surfactants listed above, the number to the left of the S indicates a hydrophobic aliphatic chain of from 11 to 15 carbon atoms derived from a mixture of alcohols on $C_{11}$ to $C_{15}$ backbone chains, and the number to the right of the S designates the average number of moles of ethylene oxide as the hydrophil. Thus for example, Tergitol 15-S-5 is a mixture of linear aliphatic alcohols in the $C_{11}$ to $C_{15}$ range ethoxylated with an average of 5 moles of ethylene oxide. All of these commercially marketed Tergitol S series of surfactants are water soluble except for Tergitol 15-S-3, which is essentially water insoluble. Mixtures of these materials can also be employed in providing the dye penetrant of the invention, such as a mixture of the above Tergitols 15-S-5 and 15-S-3; a mixture of 15-S-3 and 15-S-9; and a mixture of 15-S-5 and 15-S-9.

The above preferred class of nonionic biodegradable surfactants employed as carrier or vehicle for the dye of the penetrant solution according to the invention, are prepared by reacting an alcohol or mixture of alcohols, with the desired proportion of ethylene oxide, in the presence of an alkaline catalyst, such as potassium hydroxide. The ethylene oxide may be added to the alcohol or mixture of alcohols in one continuous step or it may be added in several steps. The products thus produced possess random distribution of oxyethylene groups, as noted above.

Another process for preparing the above nonionic surfactants in the form of ethoxylates of linear secondary aliphatic alcohols, is described in U.S. Pat. No. 2,870,220.

Although Tergitol 15-S-3 is essentially water insoluble and is usually employed in combination with the other members of the Tergitol S series noted above, such as Tergitol 15-S-5, dye penetrant compositions according to the invention containing Tergitol 15-S-3 alone, can be employed. However, Tergitol 15-S-3 has its greatest utility for production of dye penetrants having high sensitivity according to the invention, when employed in combination with the other water washable and water soluble Tergitols such as Tergitol 15-S-5 and Tergitol 15-S-9.

Dye penetrant compositions containing the above described ethoxylates of secondary aliphatic alcohols as vehicle and a dye are described in my above U.S. Pat. No. 3,915,886.

Also, particularly effective dye penetrants are provided according to the invention employing a combination or mixture of the above Tergitols 15-S-5 and 15-S-9, and to which there can be added optionally Tergitol 15-S-3, as described in my U.S. Pat. No. 3,939,092.

The nonhalogenated organic solvent additive incorporated in the dye penetrant composition for rendering the subsequent solvent-free residues LOX safe or compatible are generally liquids which are volatile at room temperature and which preferably have a boiling temperature below about 260° F at ambient pressure, and which function as a solvent for the dye penetrant components, including the oxyalkylated nonionic surfactant and the dye. Such solvents evaporate rapidly at room temperature and the solvents employed do not leave a residue. Suitable solvents are the polar solvents, which contain carbonyl or hydroxyl groups. Examples of suitable solvents are the aliphatic ketones, such as those containing from about 3 to about 6 carbon atoms, preferably about 3 to about 5 carbon atoms, such as acetone, methyl ethyl ketone, diethyl ketone, methyl isopropyl ketone, methyl n-propyl ketone, methyl isobutyl ketone, and the like. Alcohols can also be used, such as the aliphatic alcohols, e.g. containing from about 2 to about 4 carbon atoms, such as ethyl alcohol, propyl alcohol, isopropyl alcohol, n-butyl alcohol, and the like. Mixtures of such solvents also can be employed. The preferred solvents are the above noted ketones, preferably acetone and methyl ethyl ketone (MEK). There can also be employed saturated aliphatic hydrocarbons, e.g. containing from about 5 to about 8 carbon atoms such as n-pentane, n-hexane, isohexane, n-heptane, isoheptane, n-octane and isooctane, as well as mixtures thereof, e.g. petroleum naphtha, consisting chiefly of heptanes and octanes. However, such hydrocarbons are not the preferred solvents.

Of particular note, although the above nonhalogenated solvents are flammable, the residues of the dye penetrant remaining in the cracks and flaws of the part following evaporation of the solvent, do not react with liquid oxygen, and the diluted dye penetrant containing a large proportion of such flammable solvent is noncorrosive with and does not adversely affect many types of metal parts such as steel parts.

Any suitable dye generally employed in dye penetrant compositions can be incorporated into the nonionic oxyalkylated alcohol surfactants described above for producing the dye penetrant compositions employed in the invention process. Preferably, however, a fluorescent dye is employed for this purpose. The oxyalkylated surfactant vehicle for the dye is compatible therewith and has the ability to dissolve either small or relatively large amounts of the dye and to hold a high concentration of dye in solution while providing good resolution and clarity of the dye trace in the cracks and flaws.

As previously noted, the dye penetrant solution employed according to the invention preferably contains a fluorescent dye. Various types of fluorescent dyes can be employed including for example the dye marketed as Fluorol 7GA and Morton Fluorescent Yellow G, as well as other fluorescent dyes such as those marketed as Calcofluor Yellow, Axosol Brilliant Yellow 6GF; Rhodanine B, Rhodanine 6 GDN, Calcofluor White RW, Blancophor White AW, Auramine and Eosine G, and water soluble fluorescent dyes such as Blancophor FFG.

The dye penetrant composition employed according to the invention alternatively can contain non-fluorescent or daylight type dyes such as azo type dyes, e.g., xyleneazo-beta-naphthol, Mefford No. 322 dye, believed to be o-toluene-azoxyleneazo-beta-naphthol, and the azo dyes marketed as Oil Red "O" and Sudan Red. These dyes conveniently can be employed where daylight or white light is only available, and particularly where the surface of the body to be detected contains relatively gross cracks. However, it is preferred to employ fluorescent dyes having greater sensitivity or detectability as result of the high contrast obtained by the fluorescent indications.

The amount of dye which is incorporated into the oxyalkylated alcohol surfactant or carrier to produce the dye penetrant composition of the invention, can range from about 0.1 to 15, preferably about 0.5 to about 10, parts of the dye, or mixtures thereof, per 100 parts of the oxyalkylated alcohol surfactant, by weight. In preparing the dye penetrant composition employing according to the invention, the dye is simply added to the oxyalkylated alcohol carrier, in the desired proportion. The resulting dye penetrant composition has both high and low temperature stability.

The amount of nonhalogenated volatile organic solvent added to the dye penetrant constitutes a major proportion of the resulting solution. Generally, the dye penetrant including the above nonionic surfactant and dye, is diluted with such solvent in a proportion ranging from about 10 to about 40, preferably about 15 to about 25, parts of the solvent to 1 part of dye penetrant, consisting of the sum of the other components, that is oxyalkylated alcohol surfactant or surfactants, and dye, by volume, with an optimum ratio of 20 to 1 of volatile solvent to the sum of the other components, by volume. It is preferred to employ a ratio of such solvent to the sum of the other components not greater than about 30 to 1, by volume, since use of the solvent in excess of the above noted 30 to 1 ratio results in some decrease in performance and in penetrant sensitivity.

Typical dye penetrant compositions to which the nonhalogenated volatile solvent can be added according to the invention are as follows:

TABLE 1

| COMPONENTS | Compositions (Parts by Weight) | | | | | | | |
|---|---|---|---|---|---|---|---|---|
| | A | B | C | D | E | F | G | H |
| Tergitol 15-S-5 | 75 | 75 | 50 | 100 | — | 75 | — | — |
| Tergitol 15-S-9 | 25 | 25 | — | — | 100 | — | 100 | — |
| Tergitol 15-S-3 | — | — | 50 | — | — | 25 | — | — |
| Plurafac A-24 | — | — | — | 13 | — | — | — | 100 |
| Calcofluor White | | | | | | | | |

TABLE 1-continued

| COMPONENTS | Compositions (Parts by Weight) | | | | | | | |
|---|---|---|---|---|---|---|---|---|
| | A | B | C | D | E | F | G | H |
| RW | 5 | 2.5 | 5 | 5 | 2.5 | 1.25 | — | 5 |
| Fluorol 7 G A | 1.5 | 0.75 | 1.5 | .15 | .75 | .375 | — | 1.5 |
| Morton Fluorescent Yellow G | — | — | — | — | — | — | 2.5 | — |

Illustrative examples of the LOX compatible dye penetrant composition of the invention incorporating varying proportions of nonhalogenated solvent such as MEK or acetone, into the typical dye penetrant composition A of Table 1 above, are set forth in Table 2 below.

TABLE 2

| LOX compatible dye penetrant compositions (Parts by Volume) | | | | | | |
|---|---|---|---|---|---|---|
| COMPONENTS | I | II | III | IV | V | VI |
| Composition A | 1 | 1 | 1 | 1 | 1 | 1 |
| Nonhalogenated solvent | 20 | 30 | 25 | 15 | 10 | 35 |

The metal surfaces to which the dye penetrant compositions can be applied include a wide variety of metals and alloys and particularly those generally used in the aircraft industry, such as aluminum and copper, and their alloys, such as chromium plated brass, and steel alloys such as PH14-8 Mo, and the stainless series of steels, and the like.

The effectiveness or LOX compatibility of the dye penetrants of the invention is illustrated by comparative impact test measurements which determine the compatibility of the dye penetrant compositions with liquid oxygen. The following is an example of such test measurements.

EXAMPLE 1

In National Aeronautics and Space Administration specification MSFC-SPEC-106, criteria and a method is established for determining the compatability and impact sensitivity of materials with liquid and gaseous oxygen. Employing this test procedure, and utilizing the liquid dye penetrant composition I above, and containing acetone as nonhalogenated solvent, impact sensitivity tests were conducted. In these tests individual, clean, anodized aluminum 6061-T6 discs, 11/16 inch diameter were respectively soaked in the liquid dye penetrant. The discs were then allowed to drain for 15 minutes and were tested in an impact tester of the type described in the above specification. 20 specimen discs each coated with penetrant were impact tested at 72 ft.-lbs. impact, while the discs were immersed at the bottom of a precooled test cup containing liquid oxygen. If the material being tested is not compatible with liquid oxygen it will immediately explode, flash or burn. The penetrant samples were reported to be compatible with LOX at 72 ft.-lbs. impact if there were no audible explosions, no visible flash in a darkened room, and no discoloration of the aluminum specimen discs or evidence of disc charring.

The subject dye penetrant, composition I, did not react during the required 20 impact drops at 72 ft.-lbs. and successfully passed the impact test with LOX.

It is noted that the dye penetrant composition I employed in this test procedure, and incorporating composition A of Table 1 above, had a substantial amount of dye which is capable of reaction with LOX, yet by incorporating the nonhalogenated volatile solvent acetone into such composition it successfully passed the LOX compatibility test as noted above.

EXAMPLE 2

The same test procedure was carried out as in the case of Example 1 above, using the standard 20 impact drops at 72 ft.-lbs., employing the dye penetrant composition A of Table 1 above, alone, and in the absence of any nonhalogenated solvent.

The results showed 17 reactions occurred out of the 20 drops. Thus, dye penetrant composition A did not pass the test and hence is not LOX compatible.

If desired, a developer composition can be employed in conjunction with the nonhalogenated solvent containing dye penetrant composition of the invention. When employed, a dry powder or non-aqueous (volatile solvent base) developer composition can be employed, provided that when the latter type developer is employed sufficient time is given to permit evaporation of the solvent. Thus, any developer of the above types can be utilized provided they are LOX compatible, so that any remaining developer residue is non-reactive with liquid oxygen. In each case, the developer composition contains a light colored powder, forming a coating which contrasts with the color of the dye in the penetrant and which acts as a wick or blotter, and causes penetrant containing the dye, e.g. fluorescent dye, which was retained in the cracks or surface flaws, to be drawn up out of the surface defects by capillary action and to "bleed" through the powder. Exemplary developer compositions for use in conjunction with the dye penetrant composition according to the invention, are those described in my U.S. Pat. No. 3,803,051, which is a dry powder developer containing fumed alumina, fumed silica, fumed titanium dioxide and talc, and in my U.S. Pat. No. 3,748,469, and which is a wet non-aqueous developer composition consisting essentially of isopropyl alcohol, talc and glycol monobutyl ether. The descriptions of such developer compositions contained in the above patents are incorporated herein by reference.

The dye penetrant composition employed in the invention process, employing the above biodegradable nonionic oxyalkylated alcohol surfactants can be tailored to have varying degrees of sensitivity for detection of the smallest microcracks to gross cracks in a part surface by generally varying the amount of dye incorporated, and also by selecting particular surfactants or combinations thereof.

In the method for detecting cracks and flaws in the surface of an object employing the LOX compatible dye penetrant composition of the invention, such dye penetrant is applied to the part surface in any suitable manner, as by spraying. Upon application of the dye penetrant to the surface of the test part, the nonhalogenated volatile solvent evaporates very rapidly, e.g. within about 2 to about 5 seconds, although in some instances this may require a period up to about 5 minutes, and the excess dye penetrant composition is readily removed from the object surface by water washing, e.g. by application of a water spray or a sprayed mixture of air and water, or by wiping with a water moistened cloth. The dye penetrant compositions hereof, particularly these containing the above Tergitols 15-S-5 to 15-S-9, generally have excellent wetability and practically instantaneous washability with water without removing dye penetrant from the cracks and defects on the part surface, followed by drying the part surface.

If desired, a developer composition, e.g. of the types noted above, can then be applied to the part surface followed by removal of excess developer, as by means of an air blast. The part is then viewed under suitable lighting conditions, employing black light or fluorescent illumination when the dye penetrant contains a fluorescent dye.

Following inspection of the part and incorporation thereof into a device such as the propellant tanks of a rocket motor which uses liquid oxygen, any thin remaining residue of dye penetrant on the part surface or in any surface defects such as cracks, is now rendered inactive or inert with respect to LOX. Thus, it is believed that the nonhalogenated volatile solvent in some unknown manner functions to deactivate such dye penetrant residue remaining on the surface and in the surface cracks of the part, with respect to its reactivity with liquid oxygen, even though such solvents are per se flammable. However, as previously noted, unexpectedly the use of such solvent in the dye penetrant does not affect the biodegradability of the dye penetrant following evaporation of the solvent, and does not affect the sensitivity of the dye penetrant. Examples showing these results are set forth below. As previously noted, it was particularly surprising to discover that flammable solvents such as MEK and acetone can be used to provide LOX-compatible penetrants.

Where it is desired to employ a relatively insoluble nonionic surfactant in the dye penetrant composition, such as Tergitol 15-S-3 noted above, alone or in substantial proportion in admixture with another water soluble Tergitol such as Tergitol 15-S-5, in order to obtain high sensitivity, the post emulsifiable dye penetrant inspection method of my copending application Ser. No. 535,262, filed Dec. 23, 1974, now U.S. Pat. No. 3,981,185, can be employed. According to such procedure, the dye penetrant composition containing the biodegradable oxyalkylated alcohol nonionic surfactant, such as Tergitol 15-S-3 as carrier, and diluted with nonhalogenated volatile solvent according to the invention, can be applied as by dipping or spraying, preferably the latter to a test part, and the solvent evaporated, e.g. in about 1 to 5 seconds, followed by treatment of the penetrant covered parts as by spraying, with an emulsifier containing as an essential component biodegradable nonionic surfactants of the same general class as employed as carrier for the dye in the dye penetrant composition, but having greater water solubility, such as Tergitol 15-S-9. In such postemulsifiable process, the oxyalkylated alcohol nonionic surfactant in the dye penetrant can have an average value for $m$ in the formula above of about 3 to 4, and the oxyalkylated alcohol nonionic surfactant in the emulsifier can have an average value for $m$ of about 5 to 12. In order to render the dye penetrant residue compatible with liquid oxygen, in this post emulsifiable procedure the emuslifier must also contain nonhalogenated volatile solvent as above defined in combination with the above surfactant, e.g. Tergitol 15-S-9. Thus, in the emulsifier, such surfactant is diluted with the above solvent in the same proportions as the dye penetrant composition, namely about 10 to about 40, preferably about 15 to about 25, parts of the solvent to 1 part of nonionic surfactant, by volume.

The nonhalogenated solvent in the emulsifier is then allowed to evaporate, leaving a thin film of emulsifier over the initially applied penetrant. After a dwell time of about 1 to 5 minutes, the resulting emulsified penetrant is then removed from the surface of the part as by spraying with water, without dislodging the dye penetrant from the surface cracks and thus entrapping the penetrant therein, and the part surface is then dried and inspected under suitable light, e.g. ultraviolet light. If desired, a developer also can be employed following removal of the emulsified penetrant from the part surface.

The following are examples of practice of the invention.

EXAMPLE 3

A test panel of 2014 aluminum and containing microcracks uniformly distributed over the panel was divided by a groove into two equal test areas for test comparison purposes.

The fluorescent dye penetrant composition I of Table 2 above, containing acetone as solvent, was applied as by spraying, to one-half of the surface of the test panel. Almost instantaneously, that is in the matter of 2 or 3 seconds, the nonhalogenated volatile solvent evaporated, and a water wash was then applied as by an air-water spray over the coating of the dye penetrant composition I on the test panel, causing almost instantaneous washing away of the dye penetrant on the surface of the panel without dislodging the dye penetrant from the surface cracks and thus entrapping the penetrant therein. The part surface was then dried with an air blast. The washed dye penetrant removed from the part surface was biodegradable.

The procedure above was repeated, but applying the dye penetration composition A of Table 1 above, containing no acetone to the other half of the test panel surface, followed by application of a water wash under the same conditions noted above for removal of excess dye penetrant, and finally followed by drying with an air blast.

Inspection of the two penetrant treated surfaces of the test panel under ultraviolet or fluorescent light, revealed fluorescent indications from numerous readily defined microcracks therein, the fluorescent indications on both sides of the test panel being in substantially equivalent concentration, with substantially the same brightness and sensitivity or optical intensity on both sides of the test panel.

This example shows that the nonhalogenated solvent-containing dye penetrant composition of the invention, following removal of the volatile solvent, has essentially the same sensitivity or ability to disclose cracks and defects in a part surface, and the same biodegradability, as in the case of the dye penetrant composition free of such solvent, yet the former has the substantial advantage of being LOX compatible.

EXAMPLE 4

The procedure of Example 3 is repeated except that in each case, following removal of excess dye penetrant from in part surface, both halves of the test panel surface are covered with a powder developer having the following composition, according to my above U.S. Pat. No. 3,083,051.

| COMPONENTS | Percent by Weight |
|---|---|
| Talc | 52 |
| Alumina | 35 |

-continued

| COMPONENTS | Percent by Weight |
|---|---|
| Silica | 4 |
| TiO$_2$ | 9 |

The above developer is permitted to dwell over the surface of the test panel for a period of about 2 minutes.

Excess developer composition is then carefully removed from the surface of the test panel by means of a gentle air blast.

Both areas of the panel are then placed under fluorescent or ultraviolet illumination and it is again observed that a substantially equal concentration of fluorescent indications are revealed on each of the adjacent surfaces of the test panel, with substantially equivalent fluorescent brightness and sensitivity in both areas of the test specimen.

EXAMPLE 5

The procedure of Example 3 is repeated except employing in place of composition I, composition II of Table 2 above, employing methyl ethyl ketone (MEK) as solvent, at a dilution or solvent concentration, in the proportion of 25 parts of acetone to 1 part of dye penetrant composition A, by volume.

Substantially the same results are obtained as in Example 3, namely substantially equivalent concentration of fluorescent indications of cracks on both sides of the test specimen, with substantially equal brightness and sensitivity of the fluorescent indications on both test areas of the panel.

EXAMPLE 6

A fluorescent dye penetrant composition is prepared by diluting a composition containing 100 parts biodegradable Tergitol 15-S-3 as carrier, and 5 parts Calcofluor White RW and 1.5 parts Fluorol 7 G A, by weight, with acetone, in a proportion of 20 parts of acetone to 1 part of the sum of the other components, by volume.

The resulting dye penetrant composition is applied by spraying to a chrominum-plated brass test panel containing microcracks closely distributed over its entire surface.

After the acetone evaporates, the dye penetrant covered surface is sprayed with an emulsifier containing biodegradable Tergitol 15-S-9 surfactant, diluted with 20 parts acetone per 1 part of surfactant by volume. The emulsifier is allowed to dwell on the initially applied penetrant for a period of about 1 minute.

The test panel containing the emulsified penetrant, following evaporation of solvent, is then sprayed with water applied by an air-water spray over the dye penetrant-emulsifier coating, causing instantaneous washing away of the emulsified dye penetrant on the surface of the panel without dislodging the dye penetrant from the surface cracks and thus entrapping the penetrant therein, and the surface is dried by an air blast.

The test panel is then covered with a powder developer as described in Example 4.

Excess developer composition is then removed from the surface of the test panel by means of a gentle air blast.

The panel is then placed under black light (fluorescent) illumination and the above treated surface of the panel viewed in such illumination, revealing sharp and brilliant fluorescent indications from the numerous readily defined microcracks in the panel. The dye penetrant residue is compatible with liquid oxygen.

EXAMPLE 7

The procedure of Example 3 is repeated except employing a PH14-8 Mo steel surface and using composition H of Table 1 and 20 parts of volume acetone to 1 part of volume of composition H.

Results similar to those of Example 3 are obtained, with no damage or indication of attack of the steel surface.

EXAMPLE 8

The procedure of Example 3 is repeated except employing ethyl alcohol as solvent in composition 1 of Table 2.

Results similar to Example 3 are obtained.

EXAMPLE 9

The procedure of Example 3 is repeated except employing n-heptane as solvent in composition 1 of Table 2.

From the foregoing, it is seen that the invention provides a highly effective substantially biodegradable water washable dye penetrant composition whose residue is compatible with liquid oxygen, and consisting essentially of a single carrier for the dye, which is preferably fluorescent, in the form of certain biodegradable oxyalkylated alcohols, diluted with a substantial proportion of a volatile, nonhalogenated organic solvent, which is compatible with a wide variety of metal surfaces including metals which are attacked by halogenated hydrocarbons, such as steel surfaces, and which permits substantially instantaneous removal of such solvent by evaporation following application of the dye penetrant composition to a part surface, leaving an organic residue in the cracks or defects, which is non-reactive with liquid oxygen, followed by rapid removal of excess dye penetrant in a single wash operation, and further processing of the part surface in the conventional manner for viewing under suitable, e.g. fluorescent, lighting conditions, to obtain high brilliance, definition and resolution of the dye traces from cracks and flaws in the part surface, equivalent in this respect to the results obtained employing the same dye penetrant but in the absence of the nonhalogenated volatile solvent.

Since various changes and modifications of the invention will occur to and can be made readily by those skilled in the art without departing from the invention concept, the invention is not to be taken as limited except by the scope of the appended claims.

I claim:

1. A biodegradable liquid dye penetrant composition for use in non-destructive testing for detecting cracks and flaws in the surface of an object, and whose residue on the surface of said object is compatible with liquid oxygen (LOX), comprising (1) a biodegradable nonionic surfactant which consists essentially of an oxyalkylated aliphatic alcohol, or mixtures thereof, (2) a small amount of a dye soluble in said surfactant and (3) a major proportion of a nonhalogenated organic solvent having a boiling point below about 260° F at atmospheric pressure and being a solvent for said surfactant and said dye, said dye penetrant residue being rendered nonreactive to liquid oxygen upon evaporation of said solvent.

2. A dye penetrant composition as defined in claim 1, said oxyalkylated aliphatic alcohol or mixtures thereof being formed of an aliphatic primary or secondary alcohol carrying ethoxy or propoxy groups, or mixtures thereof.

3. A dye penetrant composition as defined in claim 1, said biodegradable nonionic surfactants being of the group consisting of (a) straight chain, primary, aliphatic oxyalkylated alcohols, wherein said alcohols can contain from 8 to 20 carbon atoms and the oxyalkyl groups are a mixture of ethylene oxide and propylene oxide groups, and (b) ethoxylates of linear secondary aliphatic alcohol, with the hydroxyl groups randomly distributed, the linear aliphatic portion of said alcohols being a mixture of alkyl chains containing in the range from 10 to 17 carbon atoms, and containing an average of from 3 to 12 moles of ethylene oxide.

4. A dye penetrant composition as defined in claim 3, wherein said nonionic surfactant in the dye penetrant composition is the sole liquid carrier for the dye therein.

5. A dye penetrant composition as defined in claim 1, wherein said nonhalogenated organic solvent is selected from the group consisting of aliphatic ketones and aliphatic alcohols.

6. A dye penetrant composition as defined in claim 5, said aliphatic ketones containing from about 2 to about 6 carbon atoms and said aliphatic alcohols containing from about 2 to about 4 carbon atoms.

7. A dye penetrant composition as defined in claim 3, wherein said surfactant (a) is a mixture of compounds having the formula:

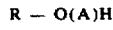

$$R - O(A)H$$

wherein R is an essentially linear alkyl group having from 10 to 18 carbon atoms, at least 70 weight percent of said compounds in said mixture having an R of from 12 to 16 carbon atoms, and A is a mixture of oxypropylene and oxyethylene groups, said oxypropylene and oxyethylene groups being from 55 to 80% of the total weight of said compounds, the oxypropylene to oxyethylene ratio of said total weight being from 0.85:1 to 2.75:1; and wherein said surfactant (b) are ethoxylates of a mixture of alcohols having the formula:

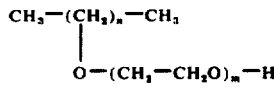

$$CH_3-(CH_2)_n-CH_3$$
$$|$$
$$O-(CH_2-CH_2O)_m-H$$

where $n$ is in the range from 9 to 13 and $m$ is an average of 3 to 12; and said dye is present in said composition in an amount ranging from about 0.1 to 15 parts, per 100 parts, by weight, of said surfactant.

8. A dye penetrant composition as defined in claim 7, wherein said nonhalogenated organic solvent is selected from the group consisting of aliphatic ketones and aliphatic alcohols, said aliphatic ketones containing from about 2 to about 6 carbon atoms and said aliphatic alcohols containing from about 2 to about 4 carbon atoms.

9. A dye penetrant composition as defined in claim 7, wherein R in said surfactant (a) can have from 12 to 18 carbon atoms, and the total number of A groups can range from about 4 to about 14; and wherein in surfactant (b) the linear alkyl hydrophobic portion of said surfactant is a mixture of $C_{11}$ to $C_{15}$ linear chains, and the hydrophilic portion of said surfactant is a polyoxyethylene chain randomly attached to the linear alkyl hydrophobic chains through an ether linkage, and wherein said surfactant (b) is selected from the group consisting of said ethoxylates of said mixture of alcohols, wherein $n$ ranges from 9 to 13, and $m$ is an average of 3, 5, 7, 9 or 12.

10. A dye penetrant composition as defined in claim 9, wherein said nonhalogenated organic solvent is selected from the group consisting of aliphatic ketones and aliphatic alcohols, said aliphatic ketones containing from about 2 to 6 carbon atoms and said aliphatic alcohols containing from about 2 to about 4 carbon atoms, said nonhalogenated organic solvent being present in an amount ranging from about 10 to about 40 parts, to 1 part of the sum of said surfactant and said dye.

11. A dye penetrant composition as defined in claim 10, wherein said dye is fluorescent dye and said nonhalogenated organic solvent is a ketone containing from about 3 to about 5 carbon atoms.

12. A dye penetrant composition as defined in claim 1, wherein said surfactant consists of ethoxylates of a mixture of alcohols having the formula:

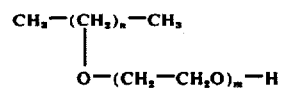

$$CH_3-(CH_2)_n-CH_3$$
$$|$$
$$O-(CH_2-CH_2O)_m-H$$

where $n$ is in the range from 9 to 13 and m is an average of 3 to 12.

13. A dye penetrant composition as defined in claim 12, wherein said surfactant is selected from the group consisting of said ethoxylates of said mixture of alcohols, wherein $n$ ranges from 9 to 13, and $m$ is an average of 3, 5, 7, 9, or 12.

14. A dye penetrant composition as defined in claim 12, wherein said dye is a fluorescent dye.

15. A dye penetrant composition as defined in claim 12, wherein said dye is a fluorescent dye and said dye is present in said composition in an amount ranging from about 0.1 to 15 parts, per 100 parts, by weight of said surfactant.

16. A dye penetrant composition as defined in claim 12, wherein said nonhalogenated organic solvent is selected from the group consisting of aliphatic ketones and aliphatic alcohols, said aliphatic ketones containing from about 2 to about 6 carbon atoms and said aliphatic alcohols containing from about 2 to about 4 carbon atoms.

17. A dye penetrant composition as defined in claim 12, said dye being a fluorescent dye, and said nonhalogenated organic solvent being a ketone selected from the group consisting of acetone and methyl ethyl ketone.

18. A dye penetrant composition as defined in claim 15, said dye being a fluorescent dye, said and nonhalogenated organic solvent being a ketone selected from the group consisting of acetone and methyl ethyl ketone.

19. A dye penetrant composition as defined in claim 12, said nonhalogenated organic solvent being present in an amount from about 10 to about 40 parts, to 1 part of the sum of said surfactant and said dye, by volume.

20. A dye penetrant composition as defined in claim 17, said nonhalogenated organic solvent being present in an amount ranging from about 10 to about 40 parts, to 1 part of the sum of said surfactant and said dye, by volume.

21. A dye penetrant composition as defined in claim 12, said nonhalogenated organic solvent being present in an amount ranging from about 15 to about 25 parts, to 1 part of the sum of said surfactant and said dye, by volume.

22. A dye penetrant composition as defined in claim 17, said nonhalogenated organic solvent being present in an amount ranging from about 15 to about 25 parts, to 1 part of the sum of said surfactant and said dye, by volume.

23. A dye penetrant composition as defined in claim 12, employing a combination of said biodegradable nonionic surfactants wherein $m$ in one of said surfactants is an average of 5 and $m$ in another of said surfactants is an average of 9.

24. A dye penetrant composition as defined in claim 22, employing a combination of said biodegradable nonionic surfactants wherein $m$ in one of said surfactants is an average of 5 and $m$ in another of said surfactants is an average of 9.

25. A biodegradable emulsifier composition for a liquid dye penetrant composition employed in nondestructive testing for detecting cracks and flaws in the surface of an object which comprises (1) a biodegradable nonionic surfactant which consists essentially of an oxyalkylated aliphatic alcohol, or mixtures thereof, said oxyalkylated aliphatic alcohol or mixtures thereof being formed of an aliphatic primary or secondary alcohol carrying ethoxy or propoxy groups, or mixtures thereof, and (2) a major proportion of a nonhalogenated organic solvent having a boiling point below about 260° F at atmospheric pressure and being a solvent for said surfactant, said solvent being present in an amount ranging from about 10 to about 40 parts, to 1 part of said nonionic surfactant, by volume.

26. a biodegradable emulsifier as defined in claim 25, said biodegradable nonionic surfactant being of the group which consists essentially of (a) a mixture of compounds having the formula:

wherein R is an essentially linear alkyl group having from 10 to 18 carbon atoms, at least 70 weight percent of said compounds in said mixture having an R of from 12 to 16 carbon atoms, and A is a mixture of oxypropylene and oxyethylene groups, said oxypropylene and oxyethylene groups being from 55 to 80% of the total weight of said compounds, the oxypropylene to oxyethylene ratio of said total weight being from 0.85:1 to 2.75:1; and (b) ethoxylates of a mixture of alcohols having the formula:

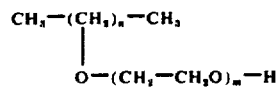

where $n$ is in the range from 9 to 13 and $m$ is an average of 5 to 12.

27. A biodegradable emulsifier composition as defined in claim 26, wherein said nonhalogenated organic solvent is selected from the group consisting of aliphatic ketones and aliphatic alcohols, said aliphatic ketones containing from about 2 to 6 carbon atoms and said aliphatic alcohols containing from about 2 to about 4 carbon atoms.

28. A biodegradable emulsifier composition as defined in claim 27, wherein said nonhalogenated organic solvent is a ketone containing from about 3 to about 5 carbon atoms, and said organic solvent being present in an amount ranging from about 15 to about 25 parts, to one part of said nonionic surfactant, by volume.

29. A biodegradable emulsifier composition as defined in claim 28, said nonhalogenated organic solvent being a ketone selected from the group consisting of acetone and methyl ethyl ketone.

30. A method for detecting cracks and flaws in the surface of an object which comprises applying to said surface a biodegradable liquid dye penetrant composition comprising (1) a biodegradable nonionic surfactant which consists essentially of an oxyalkylated aliphatic alcohol or mixtures thereof, (2) a small amount of a dye soluble in said surfactant and (3) a major proportion of a nonhalogenated organic solvent having a boiling point below about 260° F at atmospheric pressure and being a solvent for said surfactant and said dye, permitting said solvent to evaporate, removing excess dye penetrant composition from said cracks and flaws in said surface, the remaining dye penetrant residue being rendered non-reactive to liquid oxygen upon evaporation of said solvent, and viewing the surface of said object under lighting conditions to obtain colored traces from the dye in said cracks and flaws.

31. A method as defined in claim 30, said biodegradable nonionic surfactant being of the group consisting of (a) straight chain, primary, aliphatic oxyalkylated alcohols, wherein said alcohols can contain from 8 to 20 carbon atoms and the oxyalkyl groups are a mixture of ethylene oxide and propylene oxide groups, and (b) ethoxylates of linear secondary aliphatic alcohols, with the hydroxyl groups randomly distributed, the linear aliphatic portion of said alcohols being a mixture of alkyl chains containing in the range from 10 to 17 carbon atoms, and containing an average of from 3 to 12 moles of ethylene oxide.

32. A method as defined in claim 31, wherein said nonhalogenated organic solvent is selected from the group consisting of aliphatic ketones and aliphatic alcohols, said aliphatic ketones containing from about 2 to about 6 carbon atoms and said aliphatic alcohols containing from about 2 to about 4 carbon atoms.

33. A method as defined in claim 32, wherein said surfactant (a) is a mixture of compounds having the formula:

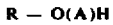

wherein R is an essentially linear alkyl group having from 10 to 18 carbon atoms, at least 70 weight percent of said compounds in said mixture having an R of from 12 to 16 carbon atoms, and A is a mixture of oxypropylene and oxyethylene groups, said oxypropylene and oxyethylene groups being from 55 to 80% of the total weight of said compounds, the oxypropylene to oxyethylene ratio of said total weight being from 0.85:1 to 2.75:1; and wherein said surfactant (b) are ethoxylates of a mixture of alcohols having the formula:

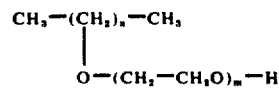

where $n$ is in the range from 9 to 13 and $m$ is an average of 3 to 12; and said dye is present in said composition in an amount ranging from about 0.1 to 15 parts, per 100 parts, by weight, of said surfactant.

34. A method as defined in claim 33, wherein said surfactant is said surfactant (b) is selected from the group consisting of said ethoxylates of said mixture of alcohols, wherein $n$ ranges from 9 to 13, and $m$ is an average of 3, 5, 7, 9, or 12.

35. A method as defined in claim 34, wherein said dye is a fluorescent dye, and said surface of said object is viewed under fluorescigenous light to obtain colored fluorescent traces from the dye in said cracks and flaws.

36. A method as defined in claim 34, wherein said dye is a fluorescent dye, and said surface of said object is viewed under fluorescigenous light to obtain colored fluorescent traces from the dye in said cracks and flaws, and said nonhalogenated organic solvent is a ketone containing from about 3 to about 5 carbon atoms.

37. A method as defined in claim 36, wherein said nonhalogenated organic solvent is present in an amount ranging from about 10 to about 40 parts, to 1 part of the sum of said surfactant and said dye, by volume.

38. A method as defined in claim 37, said organic solvent being present in an amount ranging from about 15 to about 25 parts, to 1 part of the sum of said surfactant and said dye, by volume.

39. A method as defined in claim 37, wherein said nonhalogenated organic solvent is a ketone selected from the group consisting of acetone and methyl ethyl ketone.

40. A method as defined in claim 37, and employing a combination of said biodegradable nonionic surfactants wherein $m$ in one of said surfactants is an average of 5 and $m$ in another of said surfactants is an average of 9.

41. A method as defined in claim 31, said surfactant in said dye penetrant composition having limited water solubility and rendering the dye penetrant composition after evaporation of said solvent, difficult to wash away with water, including contacting the dye penetrant covered surface after evaporation of nonhalogenated organic solvent, with an emulsifier containing as essential components a second biodegradable nonionic surfactant as above defined and a major proportion of a nonhalogenated organic solvent as above defined, said second surfactant being essentially water soluble and rendering the emulsified penetrant water washable, and after evaporation of nonhalogenated organic solvent from said emulsifier, contacting the emulsified penetrant on the surface of said object with water for removing said excess dye penetrant composition from the surface of said object, and drying said surface prior to said viewing said object.

42. A method as defined in claim 41, wherein said dye is a fluorescent dye and said dye is present in said dye penetrant composition in an amount ranging from about 0.1 to 15 parts per 100 parts, by weight of said surfactant, and said nonhalogenated solvent is preent in an amount ranging from about 10 to about 40 parts, to 1 part of the sum of said surfactant and said dye, by volume, said organic solvent being present in said emulsifier in an amount ranging from about 10 to about 40 parts, to 1 part of said second surfactant, by volume.

43. A method as defined in claim 42, wherein said surfactant consists of ethoxylates of a mixture of alcohols having the formula:

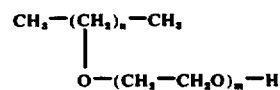

where $n$ is in the range of from 9 to 13 and $m$ is an average of 3 to 12, and wherein $m$ of said surfactant in said dye penetrant composition is an average of 3 to 4, and wherein $m$ of said surfactant in said emulsifier is an average of about 5 to 12.

44. A method as defined in claim 42, wherein said nonhalogenated organic solvent is selected from the group consisting of aliphatic ketones and aliphatic alcohols, said aliphatic ketones consisting from about 2 to about 6 carbon atoms and said aliphatic alcohols containing from about 2 to about 4 carbon atoms.

45. A method as defined in claim 43, wherein said nonhalogenated organic solvent is selected from the group consisting of acetone and methyl ethyl ketone.

46. A method as defined in claim 31, including applying a developer to said surface after removing said excess dye penetrant composition from said surface, and prior to said viewing the surface of said object.

47. A dye penetrant composition as defined in claim 1, wherein said nonhalogenated organic solvent is a saturated aliphatic hydrocarbon containing from about 5 to about 8 carbon atoms.

48. A method as defined in claim 31, wherein said nonhalogenated organic solvent is a saturated aliphatic hydrocarbon containing from about 5 to about 8 carbon atoms.

* * * * *